United States Patent [19]

Shima et al.

[11] Patent Number: 5,739,379
[45] Date of Patent: Apr. 14, 1998

[54] PROCESS FOR PRODUCING METHYL METHACRYLATE

[75] Inventors: Yoshikazu Shima; Shuji Ebata; Mariko Abe, all of Niigata, Japan

[73] Assignee: Mitsubishi Gas Chemical Company, Inc., Tokyo, Japan

[21] Appl. No.: 575,640

[22] Filed: Dec. 20, 1995

[30] Foreign Application Priority Data

Jan. 10, 1995 [JP] Japan ................................. 7-002079

[51] Int. Cl.$^6$ ................................................ C07C 67/30
[52] U.S. Cl. .................................................... 560/212
[58] Field of Search ........................................ 560/212

[56] References Cited

U.S. PATENT DOCUMENTS 5,068,399  11/1991  Naito et al. .
5,250,729  10/1993  Abe et al. .
5,371,273  12/1994  Shima et al. .

FOREIGN PATENT DOCUMENTS 0 598 243  5/1994  European Pat. Off. .

*Primary Examiner*—Paul J. Killos
*Attorney, Agent, or Firm*—Frishauf, Holtz, Goodman, Langer & Chick, P.C.

[57] ABSTRACT

A process for producing methyl methacrylate through gas-phase catalytic reaction of methyl α-hydroxyisobutyrate as the starting raw material which process comprises feeding methanol in an amount by weight of 0.1 to 3.0 times the amount of the methyl α-hydroxyisobutyrate in a reaction system and proceeding with the gas-phase catalytic reaction in the presence of a catalyst comprising a synthetic faujasite zeolite having a free alkali content of at most 0.1 milliequivalent/g or a catalyst comprising a molded product which is formed by molding a synthetic faujasite zeolite and a clay in an aqueous solution or suspension having a pH of less than 9. According to the above process, it is possible to produce methyl methacrylate in high yield over a long period of time by the use of methyl α-hydroxyisobutyrate as the starting raw material.

17 Claims, No Drawings

PROCESS FOR PRODUCING METHYL METHACRYLATE

BACKGROUND OF THE INVENTION

1. Field of the Invention

The present invention relates to a process for producing methyl methacrylate. More particularly, it pertains to a process for industrially producing methyl methacrylate by the use of methyl α-hydroxyisobutyrate as the starting raw material. Methyl methacrylate thus produced has industrially significant uses, for example, as the starting raw material for poly(methyl methacrylate) which is excellent in weather resistance and transparency, those for a variety of methacrylic acid esters, and the like.

2. Description of the Related Arts

The research group of the present inventors previously provided, in Japanese Patent Application Laid-Open No. 196,753/1990, a process for producing an α- or β-unsaturated carboxylic acid ester by subjecting an α-hydroxycarboxylic acid ester, an α-alkoxycarboxylic acid ester or an β-alkoxycarboxylic acid ester alone or the mixture thereof as starting raw materials to a dehydration or dealcoholization reaction by the use of a crystalline aluminosilicate as the catalyst. Among the crystalline aluminosilicates that were used in the above-mentioned process, X type or Y type zeolite exhibited particularly excellent catalytic activity. There is also disclosed that the crystalline aluminosilicate modified with an alkali metal and/or a platinum group element, especially the X type or Y type zeolite is effective as the catalyst in Japanese Patent Application Laid-Open Nos. 167,155/1991, 167,156/1991 and 167,157/1991. There is also disclosed, in Japanese Patent Application Laid-Open No. 157,413/1994 that the use of a transition-type synthetic faujasite zeolite having a specific lattice constant and also a specific Na content as a catalyst can maintain the catalytic activity for a long period of time.

As a result of further investigation based on the above-mentioned information, it has been found that such a problem has been raised by the use of as the catalyst, an ordinary X or Y type zeolite, or an X or Y type zeolite each modified with an alkali metal and/or a platinum group element, that the catalyst considerably deteriorates in a short period depending on the reaction conditions, thus requiring frequent regeneration thereof. Besides it was also found that the use of the transition-type synthetic faujasite zeolite as a catalyst considerably improves the frequency of regeneration, but the improvement is not sufficient, and thus need be enhanced.

The early deterioration of the catalyst makes it impossible to continue the reaction after several days to a few weeks from the start of the reaction depending upon the reaction conditions. The deteriorated catalyst can be regenerated by calcining it at a temperature higher than the reaction temperature, but frequent regeneration procedure is not favorable from the standpoint of an industrial stabilized operation.

SUMMARY OF THE INVENTION

Under such circumstances, intensive research and investigation were made by the present inventors in order to solve the above-mentioned difficulties. As a result, it has been ascertained by the present inventors that the early deterioration of the catalyst in the case of synthesizing methyl methacrylate through the gas-phase dehydration reaction by the use of methyl α-hydroxyisobutyrate as the reactive substrate and zeolite as the catalyst is due to the formation of high boiling byproducts which covers the pore inlets of the zeolite as the catalyst. Further investigation was made by the present inventors on the method of suppressing the formation of the high boiling byproducts. As a result, it has been found out by the present inventors that the formation of the high boiling byproducts is suppressed and thus the catalytic activity can be maintained for a long period of time by using methanol as a stabilizer and also using, as a catalyst, a molded product which is composed, as an effective ingredient, of a synthetic faujasite zeolite in which the free alkali content is lowered to 0.1 milliequivalent/g or less; or by using, as a catalyst, a molded product which is formed by molding a synthetic faujasite zeolite through the use of a clay whose aqueous solution or suspension has a pH of less than 9. The present invention has been accomplished on the basis of the above-mentioned finding and information.

The present invention provides, as the first aspect thereof, a process for producing methyl methacrylate through gas-phase catalytic reaction of methyl α-hydroxyisobutyrate as the starting raw material which process comprises feeding methanol in an amount by weight of 0.1 to 3.0 times the amount of the methyl α-hydroxyisobutyrate in a reaction system along therewith and proceeding with said gas-phase catalytic reaction in the presence of a catalyst comprising as an effective ingredient, a synthetic faujasite zeolite in which the free alkali content is at most 0.1 milliequivalent/g.

The present invention also provides, as the second aspect thereof, a process for producing methyl methacrylate through gas-phase catalytic reaction of methyl α-hydroxyisobutyrate as the starting raw material which process comprises feeding methanol in an amount by weight of 0.1 to 3.0 times the amount of methyl α-hydroxyisobutyrate in a reaction system along therewith and proceeding with said gas-phase catalytic reaction in the presence of a catalyst comprising a molded product which is formed by molding a synthetic faujasite zeolite through the use of a clay whose aqueous solution or suspension has a pH of less than 9.

DESCRIPTION OF THE PREFERRED EMBODIMENT

In the following the present invention will be described in detail.

The synthetic faujasite zeolite to be used as the effective ingredient of the catalyst in the present invention including the first and second aspects is classified into X type and Y type, which have the same crystalline structure but have each different chemical-composition in terms of Si/Al atomic ratio. In addition, examples of the above-mentioned synthetic faujasite zeolite include the transition type which is described in E. Dempsey, G. H. Kuhl, D. H. Olson "J. Phys. Chem.", 73,387(1969). The synthetic faujasite zeolite used in the present invention is not particularly limited but is preferably the zeolite with the almost equimolar ratio of Na to Al.

In general, a zeolite is produced by means of filtration, washing and drying of a silicate crystal which has been produced through the hydrothermal synthesis under an alkaline condition. When the washing is insufficient in the washing step, there is produced a zeolite which has a high free alkali content as defined hereinafter and in which alkaline components remain, thus causing an unfavorable result, especially in the first aspect of the present invention.

By the term "free alkali content" as used in the present specification is meant the value which is determined through calculation by the amount of 0.01 normal (N) hydrochloric acid used for titrating 50 g of water incorporated with 2.0 g of a zeolite.

There is employed a synthetic faujasite zeolite as the effective ingredient of the catalyst according to the present invention, and particularly in the first aspect of the present invention, there is employed a synthetic faujasite zeolite, preferably Na type synthetic faujasite zeolite having a free alkali content of 0.1 milliequivalent/g or less.

Such synthetic faujasite zeolite as having a free alkali content of 0.1 milliequivalent/g or less can be produced usually by sufficiently carrying out the washing with water in the foregoing washing step or by combining the washing with water and washing with a weakly acidic aqueous solution of an organic acid such as acetic acid or a mineral acid such as sulfuric acid.

With regard to the free alkali content in the synthetic faujasite zeolite, it is preferably 0.1 milliequivalent/g or less not only in the first aspect of the present invention but also in the second aspect thereof; and besides it is more preferably 0.08 or less, particularly preferably 0.05 or less in terms of milliequivalent/g in the present invention.

The synthetic faujasite zeolite of Na type or other type to be used in the process according to the present invention is usually in the form of fine powder unless it is produced as a binderless zeolite molding. The fine powder is difficult to be used as the industrial catalyst in a fixed bed, and accordingly, the zeolite is made into a molding in the form of sphere, cylinder or an other suitable form when used. In the case of producing the zeolite molding, the lack of mutual bondability among its fine powders necessitates the use of a binder to impart moderate plasticity and strength to the molding.

Examples of the binder to be used in the process of the present invention include a variety of binders such as a clay exemplified by kaolin and montomorillonite, silica sol and aluminum sol. In the present invention, especially in the second aspect thereof, a desired effect is exhibited by the use of, as a binder, a clay whose aqueous solution or suspension has a pH of at most 9, preferably at most 8.5, particularly preferably in the range of 4.0 to 8.0, said pH being defined hereinafter.

By the term "pH of the aqueous solution or suspension" as used in the present specification is meant the pH value at room temperature, of the supernatant liquid which is obtained by adding a clay to water in an amount of 2% by weight, sufficiently stirring the aqueous mixture, and thereafter allowing the mixture to stand. In addition, a pH of the aqueous solution or the suspension is sometimes abbreviated to a pH of the aqueous solution.

Examples of the preferable clay having a pH of the aqueous solution of less than 9 include a clay comprising as principal components, clay minerals such as smectite, palygorskite and kaolin and a purified product thereof, and examples of the particularly preferable clay among them include bentonite comprising smectite as a principal component, sepiolite comprising palygorskite as a principal component and a purified product thereof.

In the present invention, especially the second aspect thereof, the duration of high activity of the catalyst increases with a decrease in the amount of the clay to be used for molding the catalyst. The amount of the clay is preferably 30% or less by weight, more preferably 20% or less by weight taking into consideration the easiness of molding as well as the mechanical strength of the molded product and the like. In order to improve the moldability, it is possible to add to the clay, a molding assistant and a lubricant such as carboxymethyl cellulose, stearic acid, an alcohol, surfactant and fibers.

As an adoptable method for molding the catalyst, mention may be made of various methods such as extrusion molding, rolling granulation, tabletting molding and the like.

Methyl α-hydroxyisobutyrate to be used as the starting raw material in the present invention may be any of those that are produced by a variety of methods, and it is produced, for example, by the methanolysis of α-hydroxyisobutyramide or, as described in Japanese Patent Application Laid-Open No. 290,653/1989, by the reaction of α-hydroxyisobutyramide with methyl formate. Moreover, methyl α-hydroxyisobutyrate is obtained from the high boiling byproducts in so-called ACH process wherein methyl methacrylate is produced from acetone cyanohydrin and sulfuric acid and those in $C_4$ oxidation process wherein isobutylene is employed as the starting raw material. The methyl α-hydroxyisobutyrate which is recovered from such a high boiling byproduct usually contains methyl α- or β-methoxyisobutyrate. The catalyst in the present invention, however, is effective also for demethanolizing reaction of such homoloques and thus, the homoloques can be recovered as methyl methacrylate as well by the effect of the catalyst.

As the reaction in the process according to the present invention belongs to the gas-phase reaction by the use of the catalyst, particularly preferably the gas-phase reaction using a fixed-bed catalyst, methyl α-hydroxyisobutyrate as the starting raw material is vaporized by preheating and then fed in a reaction system such as a reactor. The vaporized material may be introduced therein alone or in combination with a diluting inert gas such as nitrogen, argon and helium. However, it is preferable to use methanol as the diluent in order to enhance the yield of methyl methacrylate. Accordingly, methanol is used as a diluent in the present invention. The proportion of methanol to be used as the diluent is 0.1 to 3.0 times, preferably 0.2 to 2.0 times, particularly preferably 0.5 to 2.0 times by weight the methyl α-hydroxyisobutyrate. The feed velocity of the starting raw material may be suitably determined according to various conditions without a specific limitaion, and the weight-based hourly space velocity is in the range of 0.1 to 5.0 $hr^{-1}$ on the basis of the total weight of methyl α-hydroxyisobutyrate as the starting raw material and methanol as the diluent per unit weight of the catalyst.

Proper setting of the reaction temperature is also important in the process of the present invention in order to suppress the byproduction of high boiling byproducts. The reaction temperature is to be suitably set in the range capable of suppressing the byproduction of the high boiling byproducts. It may be maintained at a constant temperature in the range of 230° to 300° C., but is preferably raised gradually in a specific range with the lapse of time of reaction so as to maintain the conversion efficiency of methyl α-hydroxyisobutyrate in the range of 98.0 to 99.9% in order to suppress the formation of various byproducts and at the same time, keep the catalyst activity at a proper level. A conversion efficiency thereof less than 98.0% unfavorably leads to a decrease in the selectivity to the objective methyl methacrylate due to an increase in the formation of methacrylic acid and high boiling substances, whereas that more than 99.9% resulting from the reaction at an unnecessarily high temperature frequently accelerates decompositional reaction of the starting raw material and the reaction products, thereby unfavorably resulting in the possibility of lowering the yield of methyl methacrylate and limiting the service life of the catalyst. The reaction is initiated at a temperature, without specific limitation, in the range of preferably 230° to 270° C., more preferably 240° to 260° C., and is completed at a temperature in the range of preferably 250° to 300° C., more preferably 260° to 290° C. The reaction pressure is not specifically limited, but is usually equal to or somewhat higher than atmospheric pressure.

The above-mentioned regulation of reaction temperature in the process of the present invention is necessary to compensate for the decrease with the lapse of time in the activity points due to the deposition of high boiling byproducts on the catalyst. When it is made impossible to maintain the conversion efficiency of methyl α-hydroxyisobutyrate in the range of 98.0 to 99.9% in the above-mentioned temperature range, the feed of the starting raw material is interrupted and thereafter, the catalyst is calcined in the air at a temperature at which the synthetic faujasite zeolite is not destroyed, preferably at 550° C. or lower. By the aforesaid procedure, the catalyst activity can be regenerated almost completely, thereby facilitating repeated use of the catalyst of the present invention.

The reaction liquid product obtained through the process of the present invention contains unreacted starting raw material and such byproducts as methacrylic acid, .acetone, and polymethylbenzene in addition to the objective methyl methacrylate. Such byproducts can easily be separated by the ordinary purification method such as distillation, extraction or the like.

According to the process of the present invention, by using methyl α-hydroxyisobutyrate as the starting raw material and the catalyst comprising, as an effective ingredient, the synthetic faujasite zeolite having a prescribed free alkali content or the catalyst comprising a molded product which is formed by molding a synthetic faujasite zeolite through the use of a clay whose aqueous solution has a pH of less than 9, it is made possible to produce methyl methacrylate in high yield over a long period of time, thus rendering the present invention highly valueable in the related industrial fields.

In the following, the present invention will be described in more detail with reference to examples, which however shall not be construed to limit the scope of the present invention thereto.

EXAMPLE 1

1) Preparation of catalyst: NaOH in an amount of 75.9 g was dissolved in 462.9 g of ion-exchanged water. The resultant solution was incorporated with 27.7 g of sodium aluminate (51.0% by weight of $Al_2O_3$ and 36.0% by weight of $Na_2O$) and further the mixed liquid of 333.0 g of silica sol (20% by weight of $SiO_2$) and 200.0 g of ion-exchanged water was added and allowed to stand under sufficient stirring until a homogeneous mixed slurry was obtained. The resultant mixture was placed in an autoclave and crystallized at 100° C. for 48 hours. Then, the crystallized product was allowed to cool to room temperature, filtered, sufficiently washed with water until the free alkali content reached as low as 0.01 milliequivalent/g, dried at 110° C. and calcined at 500° C. to afford 51.6 g of anhydrous zeolite. As the results of X-ray diffraction and analysis for chemical composition, the zeolite anhydride was found to be faujasite zeolite having a lattice constant of 24.86 Å and an Na/Al atomic ratio of 0.96.

The zeolite thus obtained in an amount of 20.1 g was incorporated with 5.06 g of Bengel-15 whose aqueous solution had 9.5±0.5 pH (produced by Japan Organic Clay Co., Ltd.) and 1.25 g of crystalline cellulose, followed by gradual addition of 14 g of ion-exchanged water with sufficient kneading. Subsequently, the kneaded product was extrusion-molded, dried at 110° C. and calcined at 500° C. to afford 25 g of molded cylindrical catalyst with 1.2 mm diameter and 3 to 7 mm length.

2) Evaluation of catalyst: A quartz glass tube with 15 mm inside diameter and 450 mm length was packed with 10 g of the above-molded catalyst to form a catalyst bed, the temperature of which was kept at 250° C. Then, 50% by weight solution of methyl α-hydroxyisobutyrate in methanol was fed in the catalyst bed via a preheating bed at a rate of 10 g/hr to gasify the solution. The reaction gas after 8 hours from the start of the reaction was condensed by cooling and the resultant condensate was sampled for one (1) hour. The result of analysis of the sample by GC (gas chromatography) gave 93.8% yield of methyl methacrylate.

Thereafter, the reaction temperature was gradually raised so as to maintain the conversion of methyl α-hydroxyisobutyrate in the range of 99.0 to 99.9% over a period of 40 days until it reached 280° C. The result of analysis of the product sample gave 92.0% yield of methyl methacrylate. The reaction was further continued at 280° C. and ceased after 3 days.

Subsequently, nitrogen was passed through the reaction system at 350° C. and then gradually replaced with air so as not to cause a hot spot to regenerate the catalyst by calcining it at 400° C. for 12 hours. As the result of X-ray diffraction analysis, the regenerated catalyst had a diffraction intensity at 2θ=6° of 92% of that prior to the use of the catalyst.

EXAMPLE 2

The procedure in Example 1 was repeated to proceed with the reaction except that the washing with water was discontinued on its way. The zeolite thus obtained had a free alkali content of 0.11 milliequivalent/g. Then, a molded catalyst was prepared in the same manner as in Example 1 except that Bengel-11 whose aqueous solution had 7.5±0.5 pH (purified bentonire product; produced by Japan Organic Clay Co., Ltd.) was used in place of Bengel-15. The molded catalyst thus obtained was used to proceed with the reaction. The reaction results thus obtained are given in Table 1.

EXAMPLE 3

The procedure in Example 1 was repeated to prepare a molded catalyst and proceed with the reaction except that Bengel-11 was used in place of Bengel-15. The reaction results thus obtained are given in Table 1.

EXAMPLE 4

The procedure in Example 2 was repeated except that after washing with water, washing with 0.01N aqueous solution of sulfuric acid and subsequent washing with water were carried out. The zeolite thus obtained had a free alkali content of 0.03 milliequivalent/g. Then, a molded catalyst was prepared in the same manner as in Example 2 by using 2.1g of Bengel-11. The molded catalyst thus obtained was used to proceed with the reaction. The reaction results thus obtained are given in Table 1.

EXAMPLE 5

The procedure in Example 4 was repeated to prepare a catalyst and proceed with the reaction except that Miraclay whose aqueous solution had 7 to 8 pH (purified sepiolite product; produced by Ohmi Mining Industries Co., Ltd.)

was used in place of Bengel-11. The reaction results thus obtained are given in Table 1.

Comparative Example 1

The procedure in Example 2 was repeated to prepare a catalyst and proceed with the reaction except that Bengel-15 was used in place of Bengel-11. The reaction results thus obtained are given in Table 1.

TABLE 1

| MMA yield (%) after 8 hr from the start of reaction | Reaction time (day) | Final reaction temperature (°C.) | MMA yield (%) at final reaction temperature |
| --- | --- | --- | --- |
| Example 1 | 93.8 | 43 | 280 | 92.0 |
| Example 2 | 93.8 | 40 | 275 | 92.3 |
| Example 3 | 93.6 | 55 | 270 | 92.2 |
| Example 4 | 93.8 | 70 | 267 | 92.3 |
| Example 5 | 93.8 | 70 | 267 | 92.3 |
| Comp. Example 1 | 92.8 | 30 | 285 | 91.5 |

Remarks: Comp. is Comparative

EXAMPLE 6

Synthetic faujasite zeolite having a lattice constant of 24.73 Å and a free alkali content of 0.08 milliequivalent/g was obtained by altering the chemical composition of the raw material for the catalyst and also the extent of washing with water. Then, a catalyst was prepared in the same manner as in Example 1 except that Laponite RD whose aqueous solution had pH of 9.2 to 9.7 (synthetic product similar to hectorite; produced by Laponite Industries Ltd.) was used in place of Bengel-15. The catalyst thus obtained was used to proceed with the reaction. The reaction results thus obtained are given in Table 2.

EXAMPLE 7

The Procedure in Example 6 was repeated except that washing with water was discontinued on its way. The synthetic faujasite zeolite thus obtained had a free alkali content of 0.12 milliequivalent/g. Then, a catalyst was prepared in the same manner as in Example 6 except that Miraclay was used in place of Laponite RD. The catalyst thus obtained was used to proceed with the reaction. The reaction results thus obtained are given in Table 2.

EXAMPLE 8

The procedure in Example 6 was repeated to prepare a catalyst and proceed with the reaction except that Miraclay was used in place of Laponite RD. The reaction results thus obtained are given in Table 2.

Comparative Example 2

The procedure in Example 7 was repeated to prepare a catalyst and proceed with the reaction except that Laponite RD was used in Place of Miraclay. The reaction results thus obtained are given in Table 2.

TABLE 2

| MMA yield (%) after 8 hr from the start of reaction | Reaction time (day) | Final reaction temperature (°C.) | MMA yield (%) at final reaction temperature |
| --- | --- | --- | --- |
| Example 6 | 93.3 | 20 | 290 | 91.7 |
| Example 7 | 93.1 | 18 | 290 | 91.2 |
| Example 8 | 93.7 | 27 | 290 | 92.1 |
| Comp. Example 2 | 92.3 | 6 | 290 | 82.3 |

EXAMPLE 9

Synthetic faujasite zeolite having a lattice constant of 25.00 Å and a free alkali content of 0.07 milliequivalent/g was obtained by altering the chemical composition of the raw material for the catalyst and also the extent of washing with water. Then, a catalyst was prepared in the same manner as in Example 1 except that Laponite RD was used in place of bengel-15. The catalyst thus obtained was used to proceed with the reaction. The reaction results thus obtained are given in Table 3.

EXAMPLE 10

The procedure in Example 9 was repeated except that washing with water was discontinued on its way. The synthetic faujasite zeolite thus obtained had a free alkali content of 0.11 milliequivalent/g. Then, a catalyst was prepared in the same manner as in Example 9 except that MIN-LI-GEL 400 whose aqueous solution had 7 to 8 pH (tradename of athapaljite produced in USA.) was used in place of Laponite RD. The catalyst thus obtained was used to proceed with the reaction. The reaction results thus obtained are given in Table 3.

EXAMPLE 11

The procedure in Example 9 was repeated to prepare a catalyst and proceed with the reaction except that MIN-LI-GEL 400 was used in place of Laponite RD. The reaction results thus obtained are given in Table 3.

Comparative Example 3

The procedure in Example 10 was repeated to prepare a catalyst and poroceed with the reaction except that Laponite RD was used in place of MIN-LI-GEL 400. The reaction results thus obtained are Given in Table 3.

TABLE 3

| MMA yield (%) after 8 hr from the start of reaction | Reaction time (day) | Final reaction temperature (°C.) | MMA yield (%) at final reaction temperature |
| --- | --- | --- | --- |
| Example 9 | 93.5 | 25 | 280 | 91.8 |
| Example 10 | 93.4 | 27 | 280 | 92.0 |
| Example 11 | 93.3 | 30 | 270 | 91.9 |
| Comp. Example 3 | 92.1 | 12 | 290 | 83.5 |

What is claimed is:

1. A process for producing methyl methacrylate by a gas-phase catalytic reaction of methyl α-hydroxyisobutyrate as a starting raw material, which process comprises feeding methanol in an amount by weight of 0.1 to 3.0 times the amount of the methyl α-hydroxyisobutyrate in a reaction system and proceeding with said gas-phase catalytic reaction in the presence of a catalyst comprising as an effective ingredient, a synthetic faujasite zeolite having a free alkali content of at most 0.1 milliequivalent/g.

2. A process for producing methyl methacrylate by a gas-phase catalytic reaction of methyl α-hydroxyisobutyrate as a starting raw material, which process comprises feeding methanol in an amount by weight of 0.1 to 3.0 times the amount of methyl α-hydroxyisobutyrate in a reaction system and proceeding with said gas-phase catalytic reaction in the presence of a catalyst comprising a molded product which is formed by molding a synthetic faujusite zeolite and a clay in an aqueous solution or suspension having a pH of less than 9.

3. The process according to claim 2, wherein the synthetic faujasite zeolite has a free alkali content of at most 0.1 milliequivalent/g.

4. The process according to claim 2 wherein the amount of said clay to be used for molding the synthetic faujasite zeolite is at most 20% by weight based on said zeolite.

5. The process according to claim 2 wherein said clay contains as a principal component at least one member selected from the group consisting of smectite and palygorskite.

6. The process according to claim 2 wherein said clay is at least one member selected from the group consisting of bentonite and sepiolite.

7. The process according to claim 1 wherein the catalyst comprises a molded product which is formed by molding a synthetic faujasite zeolite and a clay.

8. The process according to claim 1 wherein the free alkali content is at most 0.08 milliequivalent/g.

9. The process according to claim 1 wherein the free alkali content is at most 0.05 milliequivalent/g.

10. The process according to claim 1, wherein the methanol is in an amount of 0.2 to 2.0 times the amount of the methyl α-hydroxyisobutyrate.

11. The process of claim 9 wherein the methanol is in an amount of 0.5 to 2.0 times the amount of the methyl α-hydroxyisobutyrate.

12. The process of claim 11 wherein the process is carried out at a temperature of 230° to 300° C.

13. The process of claim 12 wherein the process is carried out at a weight-based hourly space velocity of 0.1 to 5.0 hour$^{-1}$ on the basis of the total weight of methyl α-hydroxyisobutyrate and methanol per unit weight of the catalyst.

14. The process of claim 2 wherein the pH is at most 8.5.

15. The process of claim 2 wherein the pH is 4.0 to 8.0.

16. The process of claim 15 wherein the zeolite is zeolite X.

17. The process of claim 15 wherein the zeolite is zeolite Y.

* * * * *